United States Patent
Mochizuki et al.

(10) Patent No.: US 9,821,814 B2
(45) Date of Patent: Nov. 21, 2017

(54) DEVICE AND METHOD FOR DETERMINING DROWSINESS AND NON-TRANSITORY STORAGE MEDIUM

(71) Applicant: Panasonic Intellectual Property Management Co., Ltd., Osaka (JP)

(72) Inventors: Makoto Mochizuki, Kanagawa (JP); Yuko Arai, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/183,814

(22) Filed: Jun. 16, 2016

(65) Prior Publication Data

US 2017/0021836 A1  Jan. 26, 2017

(30) Foreign Application Priority Data

Jul. 23, 2015 (JP) .................................. 2015-145756

(51) Int. Cl.
*B60W 40/08* (2012.01)
*B60C 9/00* (2006.01)
(Continued)

(52) U.S. Cl.
CPC ........... *B60W 40/08* (2013.01); *A61B 5/1114* (2013.01); *A61B 5/18* (2013.01); *B60C 9/00* (2013.01);
(Continued)

(58) Field of Classification Search
CPC .......... G08B 21/02; G08B 21/06; A61B 5/18; B60K 28/06; B60K 28/066; B60W 50/08;
(Continued)

(56) References Cited

U.S. PATENT DOCUMENTS 9,073,430 B1 * 7/2015 Boss ..................... B60K 28/06
2008/0180257 A1   7/2008 Omi et al.
(Continued)

FOREIGN PATENT DOCUMENTS

JP      2010-128649      6/2010

OTHER PUBLICATIONS

The Extended European Search Report dated Dec. 20, 2016 for the European Patent Application No. 16174574.0.

*Primary Examiner* — Andrew Bee
(74) *Attorney, Agent, or Firm* — Greenblum & Bernstein, P.L.C.

(57) ABSTRACT

A drowsiness determination device includes an input unit that receives vehicle information indicating the amount of variation in an attitude of a vehicle with respect to a road surface and head information indicating the amount of movement of a head of an occupant with respect to a predetermined position and a determination unit that determines whether the occupant is drowsy, on the basis of the vehicle information and the head information. The determination unit determines that the occupant is drowsy, on the conditions that when the vehicle attitude varies, the occupant head moves in the same direction as the direction in which the vehicle attitude has varied and that a delay time between the timing when the vehicle attitude has varied and the timing when the occupant head has moved is longer than a predetermined time.

9 Claims, 10 Drawing Sheets

(51) Int. Cl.
  *G08B 21/06* (2006.01)
  *A61B 5/18* (2006.01)
  *B60K 28/06* (2006.01)
  *A61B 5/11* (2006.01)
  *G08B 29/18* (2006.01)

(52) U.S. Cl.
  CPC ............ *B60K 28/066* (2013.01); *G08B 21/06* (2013.01); *B60W 2040/0827* (2013.01); *B60W 2520/00* (2013.01); *G08B 29/183* (2013.01)

(58) Field of Classification Search
  CPC ................ B60W 50/14; B60W 40/08; B60W 2040/0818; B60W 2040/0827; B60W 2040/0872; G06K 9/00832; G06K 9/00845
  See application file for complete search history.

(56) References Cited

U.S. PATENT DOCUMENTS

2010/0265074 A1* 10/2010 Namba .............. G06K 9/00771
  340/576
2015/0061875 A1  3/2015 Yang et al.

\* cited by examiner

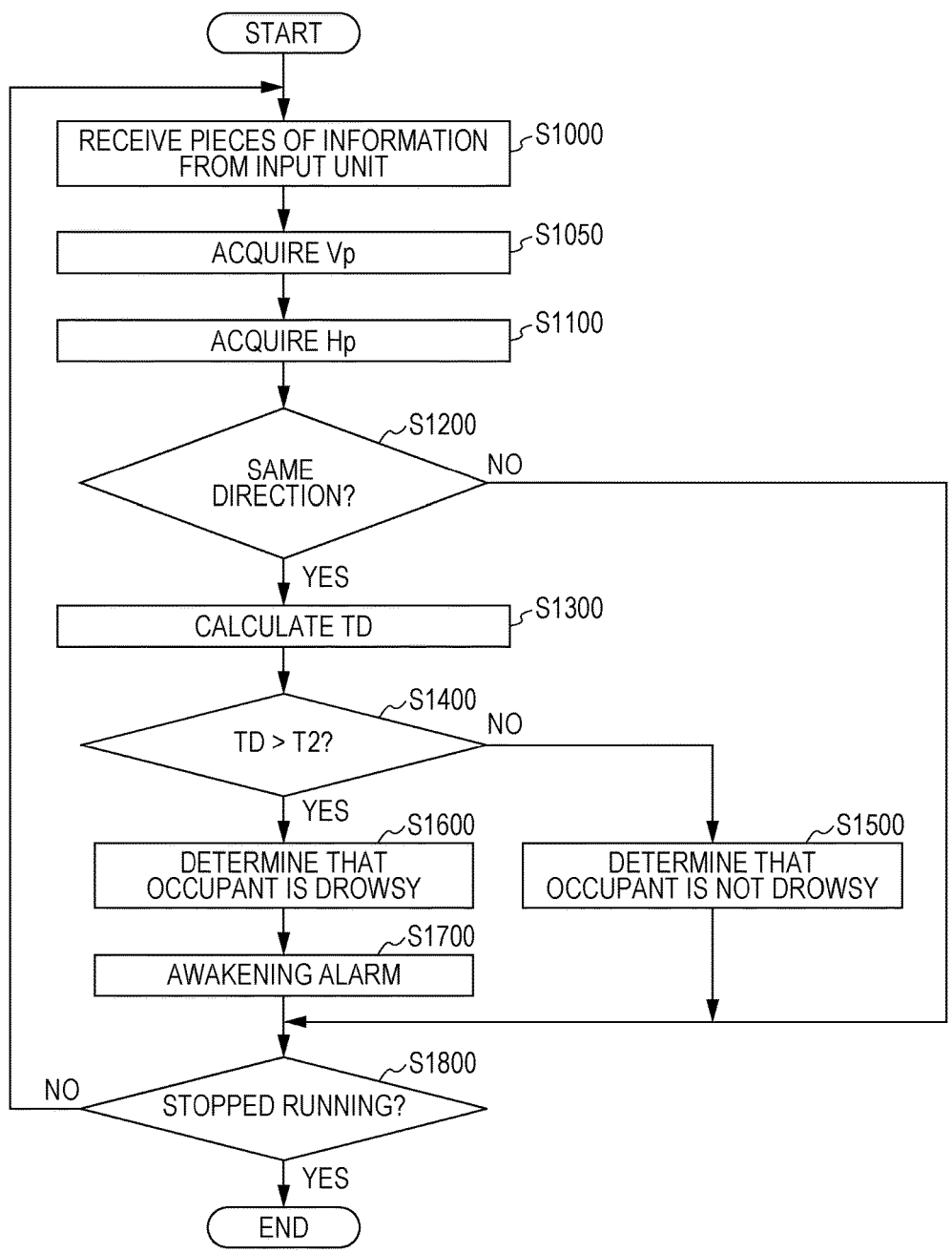

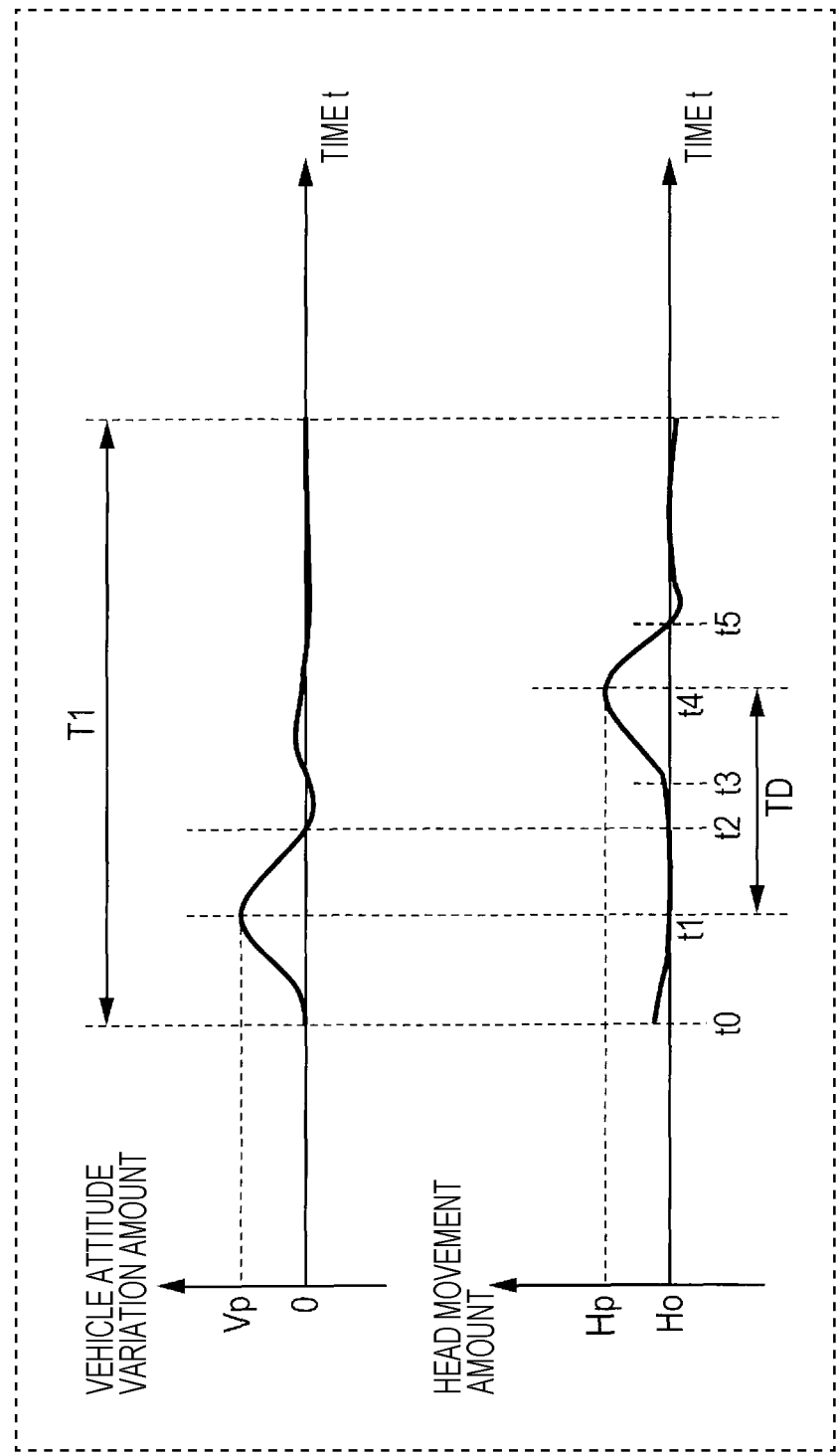

FIG. 7

| DELAY TIME | DROWSINESS LEVEL |
|---|---|
| TD < R1 | LEVEL 1 |
| R1 ≤ TD < R2 | LEVEL 2 |
| R2 ≤ TD < R3 | LEVEL 3 |
| R3 ≤ TD < R4 | LEVEL 4 |
| R4 ≤ TD | LEVEL 5 |

DEVICE AND METHOD FOR DETERMINING DROWSINESS AND NON-TRANSITORY STORAGE MEDIUM

BACKGROUND

1. Technical Field

The present disclosure relates to a drowsiness determination device and method for determining the drowsy state of an occupant and a non-transitory storage medium storing a drowsiness determination program.

2. Description of the Related Art

There have been known drowsiness determination devices that determine the drowsy state of an occupant (for example, see Japanese Patent No. 5326521). Japanese Patent No. 5326521 determines the drowsy state of an occupant on the basis of the movement of the head of the occupant in a curved section.

SUMMARY

However, Japanese Patent No. 5326521 cannot accurately determine the drowsy state of the occupant on a monotonous road, on which the head of the occupant moves to a small extent.

One non-limiting and exemplary embodiment provides a drowsiness determination device and method that can accurately determine the drowsy state of the occupant.

In one general aspect, the techniques disclosed here feature a drowsiness determination device including an input unit that receives vehicle information indicating the amount of variation in an attitude of a vehicle with respect to a road surface and head information indicating the amount of movement of a head of an occupant with respect to a predetermined position and a determination unit that determines whether the occupant is drowsy, on the basis of the vehicle information and the head information. The determination unit determines that the occupant is drowsy, on the conditions that when the vehicle attitude varies, the occupant head moves in the same direction as the direction in which the vehicle attitude has varied and that a delay time between the timing when the vehicle attitude has varied and the timing when the occupant head has moved is longer than a predetermined time.

According to the aspect of the present disclosure, the drowsy state of the occupant can be accurately determined even on a monotonous road, on which the head moves to a small extent.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 2 is a flowchart showing an example of the operation of the drowsiness determination device of the first embodiment;

FIG. 4 is a time chart showing an example of temporal variations in the amount of variation in the vehicle attitude and the amount of movement of the occupant head according to the first embodiment;

FIG. 7 is a diagram showing details of a drowsiness determination table of a first modification;

DETAILED DESCRIPTION

First Embodiment

Now, a first embodiment of the present disclosure will be described in detail with reference to the drawings.

First, there will be described the configuration of a drowsiness determination system including a drowsiness determination device of the first embodiment of the present disclosure.

Figure 1:
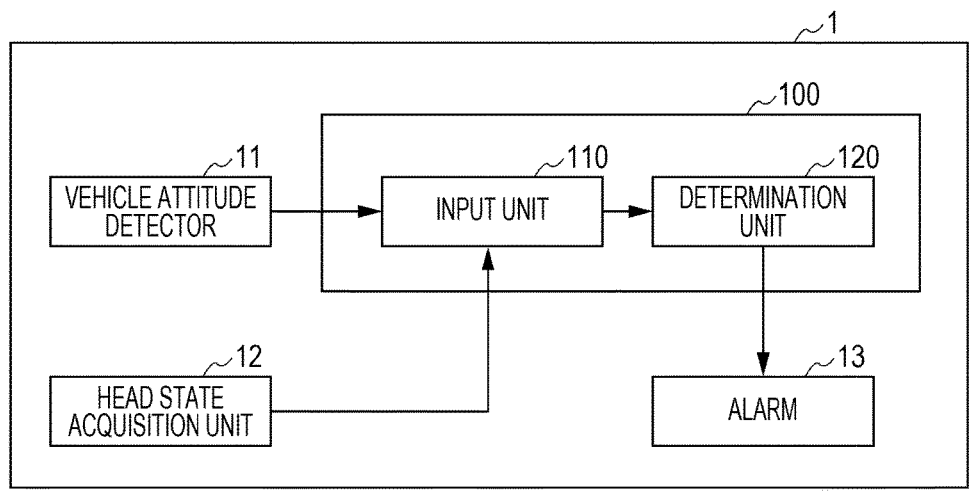
FIG. 1 is a block diagram showing an example of the configuration of a drowsiness determination system including a drowsiness determination device of a first embodiment.

FIG. 1 is a block diagram showing an example of the configuration of the drowsiness determination system including the drowsiness determination device of the present embodiment.

For example, a drowsiness determination system 1 is a system that is used in a moving object such as a vehicle and supports the operation of the vehicle. The drowsiness determination system 1 may be a vehicle-mounted device or may be a device that the user carries onto a vehicle. In the present embodiment, an example in which the user is an occupant of a vehicle, particularly, the driver of a vehicle will be described. However, the user need not be an occupant or driver of a vehicle.

As shown in FIG. 1, the drowsiness determination system 1 includes a vehicle attitude detector 11, a head state acquisition unit 12, an alarm 13, and a drowsiness determination device 100.

The vehicle attitude detector 11 is a sensor that detects the amount of variation in the attitude of a vehicle with respect to the road surface. It outputs vehicle information indicating the amount of variation to the drowsiness determination device 100 [an input unit 110 (to be discussed later)]. The amount of variation in the vehicle attitude is the size of the pitch angle, roll angle, and yaw angle of the vehicle with respect to the road surface. Note that the amount of variation in the vehicle attitude is not limited thereto and may be, for example, the distance between an edge of the vehicle body and the road surface.

The head state acquisition unit 12 is a sensor that acquires the amount of movement of the head of an occupant with respect to a predetermined position. It outputs head information indicating the amount of movement to the drowsiness determination device 100 (the input unit 110). The predetermined position may be, for example, the position of a headrest or the position of a side door. Note that the predetermined position is not limited thereto and may be changed as necessary.

The alarm 13 receives an alarm command from the drowsiness determination device 100 [a determination unit 120 (to be discussed later)] and gives, to the occupant, an alarm for awakening the occupant, for example, by emitting an alarming sound.

The drowsiness determination device 100 is a device that determines whether the occupant is drowsy, on the basis of the vehicle information and head information. It includes the input unit 110 and determination unit 120.

The input unit 110 receives vehicle information from the vehicle attitude detector 11 and outputs it to the determination unit 120. The input unit 110 also receives head information from the head state acquisition unit 12 and outputs it to the determination unit 120.

The determination unit 120 receives the vehicle information and head information from the input unit 110. The determination unit 120 stores vehicle information and head information from time T-T1, which precedes the current time T by a predetermined time T1, to the current time T. When it receives the latest vehicle information and head information, the determination unit 120 deletes the earliest vehicle information and head information. Preferably, the predetermined time T1 is set to a sufficiently long time (e.g., 10 seconds) so that the determination unit 120 can determine whether the occupant is drowsy after it recognizes a variation in the vehicle attitude.

The determination unit 120 determines whether the occupant is drowsy, on the basis of the vehicle and head information corresponding to the predetermined time T1.

Specifically, when the vehicle attitude varies, the determination unit 120 determines whether the head of the occupant has moved in the same direction as the direction in which the vehicle attitude has varied. On the condition that the occupant head has moved in the same direction as the direction in which the vehicle attitude has varied, the determination unit 120 calculates the delay time TD between the timing when the vehicle attitude has varied and the timing when the occupant head has moved. The determination unit 120 then determines whether the delay time TD is longer than a predetermined time T2. On the condition that the delay time TD is longer than the predetermined time T2, the determination unit 120 determines that the occupant is drowsy.

The delay time TD is a time corresponding to the time difference between the timing when the amount of variation in the vehicle attitude has reached a peak and the timing when the amount of movement of the occupant head has reached a peak. Note that the delay time TD is not limited thereto and may be, for example, the time difference between the timing when the vehicle attitude has just varied and the timing when the occupant head has just moved. The predetermined time T2 is a time serving as a threshold for determining whether the occupant is drowsy, in the delay time TD. It can be set to an appropriate value on the basis of an experiment result or the like.

If the determination unit 120 determines that the occupant is drowsy, it outputs an alarm command to the alarm 13.

Next, the operation of the drowsiness determination device 100 will be described.

FIG. 2 is a flowchart showing an example of the operation of the drowsiness determination device 100.

As shown in FIG. 2, when a vehicle 1A starts to run, the determination unit 120, in step S1000, receives vehicle information and head information from the input unit 110 and stores them. After step S1000, the determination unit 120 proceeds to step S1050.

In step S1050, the determination unit 120 acquires Vp [deg], which is the peak value of the amount of variation in the vehicle attitude. After step S1050, the determination unit 120 proceeds to step S1100.

In step S1100, the determination unit 120 acquires Hp [cm], which is the peak value of the amount of movement of the occupant head. After step S1100, the determination unit 120 proceeds to step S1200.

In step S1200, the determination unit 120 determines whether the direction of the variation in the vehicle attitude and the direction of the movement of the head are the same. If it determines that the variation direction and movement direction are not the same (S1200: NO), the determination unit 120 does not make a determination on the drowsiness of the occupant and proceeds to step S1800. If it determines that the variation direction and movement direction are the same (S1200: YES), the determination unit 120 proceeds to step S1300.

In step S1300, the determination unit 120 calculates the delay time TD between the timing when the vehicle attitude has varied and the timing when the occupant head has moved. After step S1300, the determination unit 120 proceeds to step S1400.

In step S1400, the determination unit 120 determines whether the delay time TD is longer than the predetermined time T2. If it determines that the delay time TD is equal to or shorter than the predetermined time T2 (S1400: NO), the determination unit 120 proceeds to step S1500. If it determines that the delay time TD is longer than the predetermined time T2 (S1400: YES), the determination unit 120 proceeds to step S1600.

In step S1500, the determination unit 120 determines that the occupant is not drowsy. After step S1500, the determination unit 120 proceeds to step S1800.

In step S1600, the determination unit 120 determines that the occupant is drowsy. After step S1600, the determination unit 120 proceeds to step S1700.

In step S1700, the determination unit 120 outputs an alarm command to the alarm 13. Thus, the alarm 13 gives, to the occupant, an alarm for awakening the occupant. After step S1700, the determination unit 120 proceeds to step S1800.

In step S1800, the determination unit 120 determines whether the vehicle has stopped running. If it determines that the vehicle has not stopped running (S1800: NO), the determination unit 120 returns to step S1000. If it determines that the vehicle has stopped running (S1800: YES), the determination unit 120 ends the process.

Effects of the drowsiness determination device 100 thus configured will be described in detail. First, referring to FIGS. 3A, 3B and 4, there will be described a case in which the occupant head moves within a predetermined time T1 from the timing when the vehicle attitude has varied and in which the direction of the variation in the vehicle attitude and the direction of the movement of the occupant head are the same (the pitch direction with respect to the road surface).

Figure 3A:
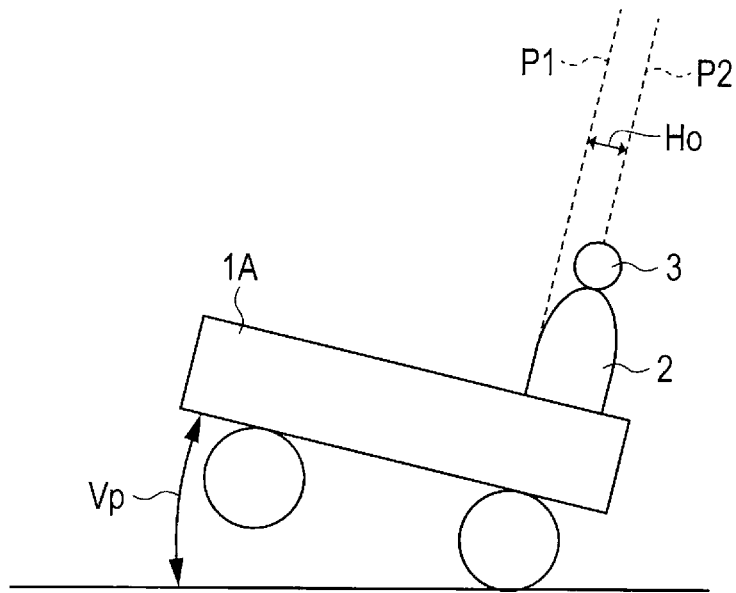
FIG. 3A is a diagram showing an example of the attitude of a vehicle and the state of the head of a occupant at the timing when the amount of variation in the vehicle attitude has reached a peak.
Figure 3B:
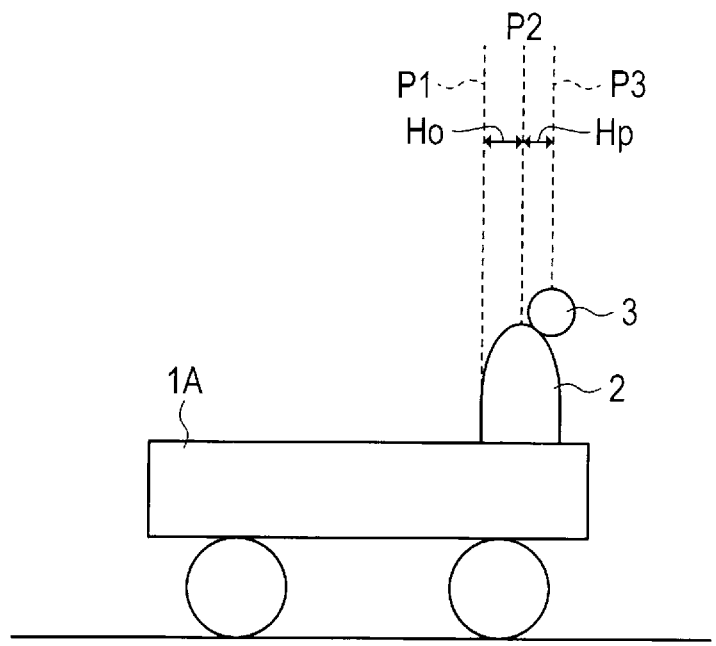
FIG. 3B is a diagram showing an example of the vehicle attitude and the state of the occupant head at the timing when the amount of movement of the occupant head has reached a peak.

FIG. 3A is a diagram showing an example of the vehicle attitude and the state of the occupant head at the timing when the amount of variation in the vehicle attitude has reached a peak. FIG. 3B is a diagram showing an example of the vehicle attitude and the state of the occupant head at the timing when, after the amount of variation in the vehicle attitude has reached a peak, the amount of movement of the occupant head caused by the variation in the vehicle attitude has reached a peak. FIG. 4 is a time chart showing an example of temporal changes in the amount of variation in the vehicle attitude and the amount of movement of the occupant head.

As shown in FIGS. 3A and 3B, when the vehicle 1A is running to the right of the diagram and when the attitude of the vehicle 1A varies in the pitch direction with respect to the road surface due, for example, to the acceleration or deceleration of the vehicle 1A or a change in the road surface state, the head 3 of an occupant 2 is tilted in the running direction in such a manner to follow the variation in the vehicle attitude of the vehicle 1A. Specifically, the head 3 of the occupant 2 moves from an initial position P2 to a peak position P3 in which the amount of variation from the initial position P2 reaches a peak value of Hp [cm]. The initial position P2 is away from a predetermined position P1 by Ho [cm], and the predetermined position P1 is the position of the headrest. While, in the present embodiment, the starting point of the movement of the head is the upper edge of the head 3 of the occupant 2, the starting point is not limited thereto and may be any other position of the head 3.

The drowsiness determination device 100 receives vehicle information and head information shown in FIGS. 3A and 3B from the vehicle attitude detector 11 and head state acquisition unit 12 and stores waveforms indicating temporal changes in the amount of variation in the vehicle attitude and the amount of movement of the head. As shown in FIG. 4, the determination unit 120 stores a waveform indicating temporal changes in the amount of variation in the vehicle attitude and having a mountainous portion (time t0 to time t2) whose peak value is Vp [deg]. The determination unit 120 also stores a waveform indicating temporal changes in the amount of movement of the occupant head and having a mountainous portion (time t3 to time t5) whose peak value is Hp. Note that the determination unit 120 need not store waveforms indicating temporal variations in the amount of the variation or movement and only has to store information indicating the direction of the variation or movement and the timing when the amount of the variation or movement has reached a peak, which is required to determine drowsiness.

The drowsiness determination device 100 identifies the timing when the amount of variation in the vehicle attitude has reached a peak and the timing when the amount of movement of the head has reached a peak, determines whether the direction of the variation and the direction of the movement are the same, and calculates the delay time TD, which is a time from time t1 when the amount of variation in the vehicle attitude has reached a peak to time t4 when the amount of movement of the head has reached a peak.

When the occupant 2 is not drowsy and when the vehicle attitude varies, the occupant 2 makes a reflex to maintain his or her attitude. Specifically, when the occupant 2 is not drowsy, the occupant 2 immediately moves the head 3 in such a manner to follow the variation in the vehicle attitude. Accordingly, the delay time TD between the variation in the attitude of the vehicle 1A and the movement of the head 3 of the occupant 2 is short. On the other hand, when the occupant 2 is drowsy, the occupant 2 impairs the function of maintaining his or her attitude and is delayed in moving the head 3 in such a manner to follow the variation in the vehicle attitude. Accordingly, the delay time TD between the variation in the attitude of the vehicle 1A and the movement of the head 3 of the occupant 2 is long.

The drowsiness determination device 100 of the present embodiment determines that the occupant 2 is drowsy, on the conditions that when the vehicle attitude varies, the head 3 of the occupant 2 has moved in the same direction as the direction in which the vehicle attitude has varied and that the delay time TD between the timing when the vehicle attitude has varied and the timing when the head 3 of the occupant 2 has moved is longer than the predetermined time T2. Thus, the drowsiness determination device 100 can accurately detect that the occupant 2 is being delayed in moving the head 3 in such a manner to follow the variation in the vehicle attitude. As a result, the drowsiness determination device 100 can accurately determine the drowsy state of the occupant 2.

As described above, the drowsiness determination device 100 of the present embodiment determines the drowsiness of the occupant 2 by comparing the delay time TD between the variation in the vehicle attitude and the movement of the head 3 with the predetermined time T2. Thus, even when the amount of the variation in the vehicle attitude and the amount of the movement of the head 3 are small, that is, even when the vehicle is traveling a monotonous road, on which the head 3 moves to a small extent, the drowsiness determination device 100 can accurately determines the drowsy state of the occupant 2.

When the determination unit 120 determines that the occupant 2 is drowsy, the determination unit 120 outputs an alarm command to the alarm 13. Thus, the occupant 2 can be awakened.

Second Embodiment

Next, a drowsiness determination device 100 of a second embodiment will be described in detail with reference to the drawings. Elements similar to those in the first embodiment are given the same reference signs and will not be described.

Figure 5:
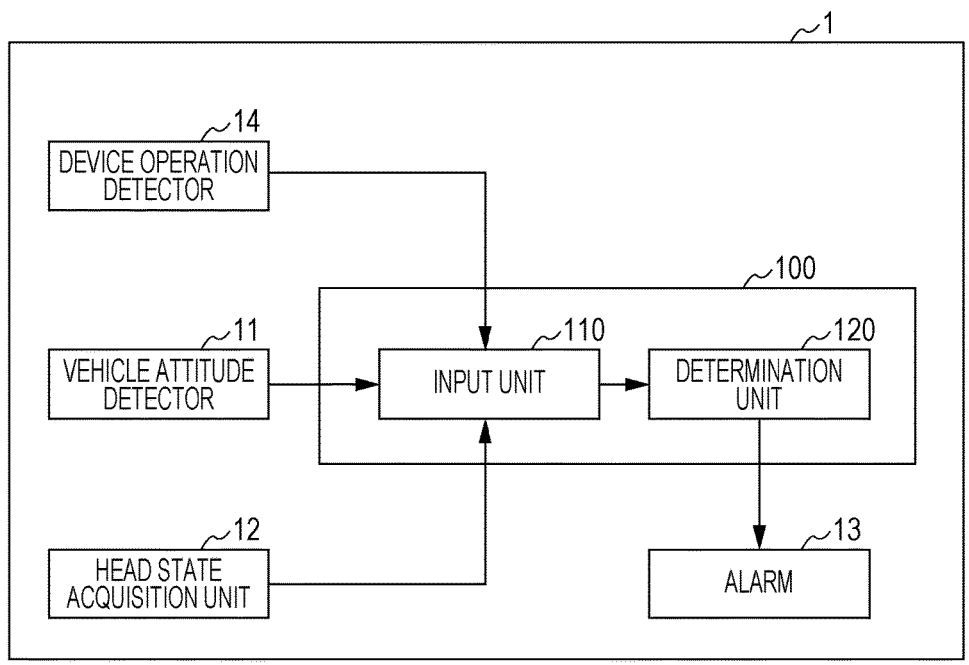
FIG. 5 is a block diagram showing an example of the configuration of a drowsiness determination system including a drowsiness determination device of a second embodiment.

FIG. 5 is a block diagram showing an example of the configuration of a vehicle including the drowsiness determination device of the second embodiment.

As shown in FIG. 5, a drowsiness determination system 1 includes elements similar to those in the first embodiment, as well as a device operation detector 14.

The device operation detector 14 is a sensor that detects operation information indicating that an occupant has inputted an operation of a vehicle-mounted device such as a car navigation system. It outputs the operation information to an input unit 110.

The input unit 110 receives the operation information from the device operation detector 14 and outputs it to a determination unit 120. The device operation detector 14 may detect a device operation on the basis of information about input to a car navigation system or the like or may detect a device operation by capturing an image of the occupant using a camera disposed in the vehicle and determining whether the occupant has operated a car navigation system or the like, by image processing.

The determination unit 120 receives the operation information from the input unit 110 and determines whether the occupant has inputted an operation of the vehicle-mounted device within a second predetermined time from the timing when the vehicle attitude has varied, on the basis of the operation information. If it determines that the occupant has not inputted an operation of the vehicle-mounted device within the second predetermined time, the determination unit 120 determines that the occupant is drowsy.

Next, the operation of the drowsiness determination device 100 of the second embodiment will be described.

Figure 6:
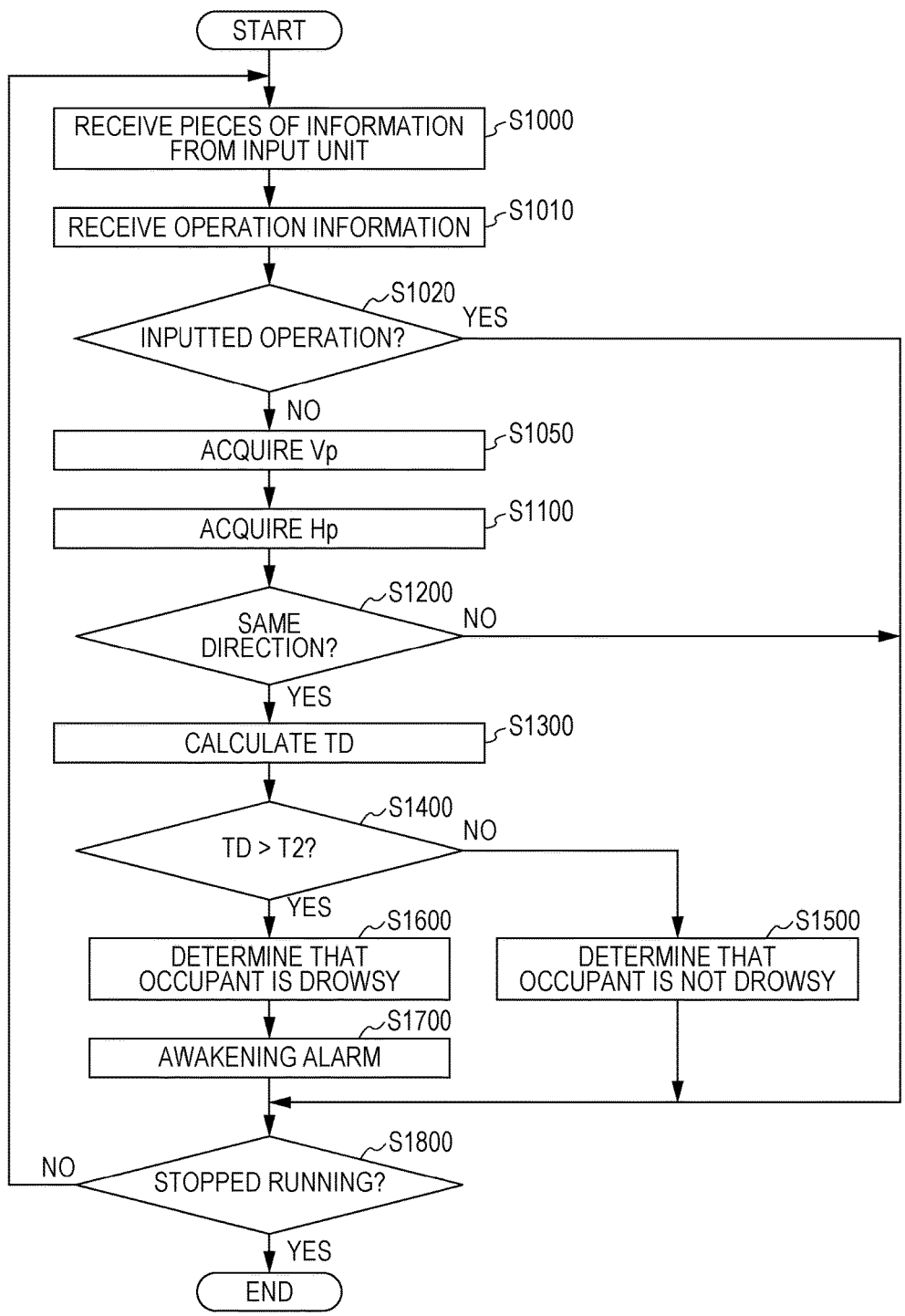
FIG. 6 is a flowchart showing an example of the operation of the drowsiness determination device of the second embodiment.

FIG. 6 is a flowchart showing an example of the operation of the drowsiness determination device 100 of the second embodiment.

As shown in FIG. 6, in step S1000, the determination unit 120 receives vehicle information and head information from the input unit 110 and then, in step S1010, receives operation information from the device operation detector 14. After step S1010, the determination unit 120 proceeds to step S1020.

In step S1020, the determination unit 120 determines whether the occupant has inputted an operation of the car navigation system, on the basis of the operation information received. If it determines that the occupant has inputted an operation (S1020: YES), the determination unit 120 proceeds to step S1800; if it determines that the occupant has not inputted an operation (S1020: NO), it proceeds to step S1050. Steps after step S1050 are similar to those in FIG. 2.

According to this configuration, when the occupant operates the vehicle-mounted device and thus moves his or her head, the drowsiness determination device 100 can be prevented from erroneously determining that the occupant is drowsy. While, in the present embodiment, the drowsiness determination device 100 determines whether it is necessary to make a determination on whether the occupant is drowsy, on the basis of information on whether the occupant has inputted an operation of the vehicle-mounted device, it may use other information. For example, the drowsiness determination device 100 may determine whether it is necessary to make a determination on whether the occupant is drowsy, on the basis of information on whether the occupant has performed an intentional operation accompanied by the movement of the head, such as checking of an obstruction around the vehicle.

While the embodiments of the present disclosure have been described, the present disclosure is not limited thereto. Various modifications can be made to the embodiments as necessary.

Modification 1

While, in the embodiments, the determination unit 120 only determines whether the occupant is drowsy, it may determine the drowsiness level from multiple levels on the basis of the delay time TD. Specifically, a determination unit 120 refers to a drowsiness determination table shown in FIG. 7 and determines the drowsiness level on the basis of a calculated delay time TD.

FIG. 7 is a diagram showing an example of details of the drowsiness determination table.

As shown in FIG. 7, the drowsiness determination table is a table in which predetermined multiple drowsiness levels and ranges of the delay time corresponding to the drowsiness levels are described.

Parameters R1 to R4 described in the ranges of the delay time are thresholds defining the ranges of the delay time TD corresponding to the drowsiness levels and satisfy a relationship $R1<R2<R3<R4$.

"Level 1" to "level 5" described as the drowsiness levels are five drowsiness levels described in Japanese Unexamined Patent Application Publication No. 2013-81516. "Level 1" corresponds to a state in which the occupant is not drowsy at all; "Level 2" corresponds to a state in which the occupant is rather drowsy; "Level 3" corresponds to a state in which the occupant is drowsy; "Level 4" corresponds to a state in which the occupant is very drowsy; and "Level 5" corresponds to a state in which the occupant is extremely drowsy.

That is, in the drowsiness determination table, higher drowsiness levels are associated with longer delay times. According to this configuration, even when the drowsiness is an initial level, the drowsiness level can be accurately determined.

In this case, preferably, the alarm 13 shown in FIG. 5 gives alarms corresponding to the drowsiness levels, for example, outputs a larger awakening sound as the drowsiness level is increased. The alarm 13 may give different alarms in accordance with the drowsiness levels as follows: when the drowsiness level is low, it uses an awakening sound like "pi"; and when the drowsiness level is high, it uses an awakening sound like "pi, pi, pi." Depending on the drowsiness level, the alarm 13 may further use other means, such as the vibration of the seat belt or an air blast using the air-conditioner, in combination with auditory information. According to this configuration, the occupant can be alarmed in a suitable manner by giving an alarm corresponding to the drowsiness level.

Modification 2

While the drowsiness determination device 100 of the first embodiment calculates the delay time TD on the basis of the timing when the amount of variation in the vehicle attitude has reached a peak and the timing when the amount of movement of the occupant head has reached a peak, the delay time TD may be calculated using other types of information in the present disclosure. For example, the drowsiness determination device 100 may calculate the delay time TD on the basis of the cross-correlation between the amount of variation in the vehicle attitude and the amount of movement of the head.

Next, the operation of a drowsiness determination device 100 that calculates the delay time TD in this manner will be described.

Figure 8:
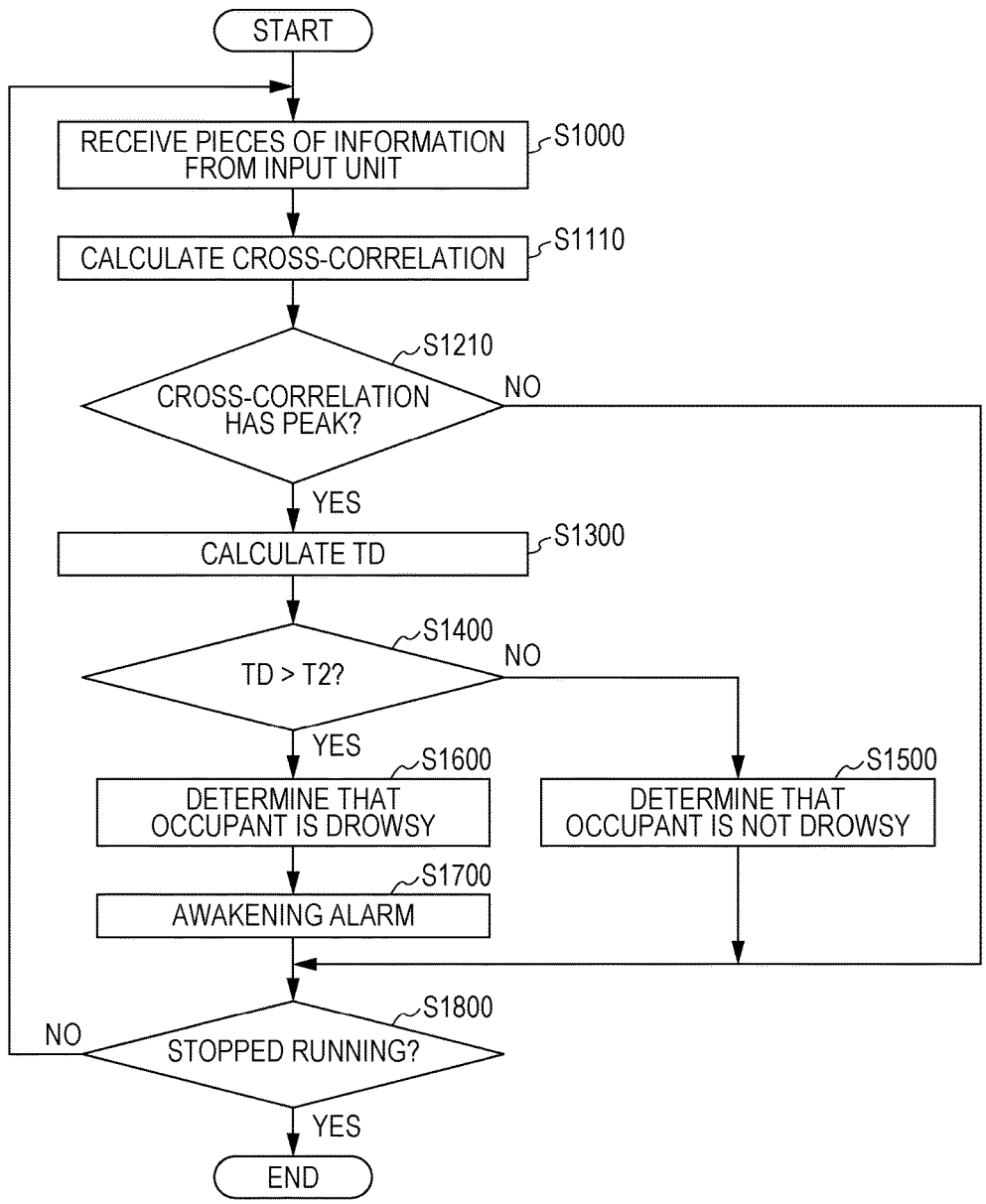
FIG. 8 is a flowchart showing an example of the operation of a drowsiness determination device of a second modification.

FIG. 8 is a flowchart showing an example of the operation of a drowsiness determination device 100 of a second modification.

As shown in FIG. 8, in step S1000, a determination unit 120 receives vehicle information and head information from an input unit 110 and, in step S1110, calculates a correlation value based on the cross-correlation between these pieces of information. After step S1110, the determination unit 120 proceeds to step S1210.

In step S1210, the determination unit 120 determines whether the correlation value based on the cross-correlation has a peak. If it determines that the correlation value has no peak (S1210: YES), the determination unit 120 proceeds to step S1800; if it determines that the correlation value has a peak (S1210: YES), it proceeds to step S1300.

In step S1300, the determination unit 120 calculates the peak of the correlation value as the delay time TD and proceeds to step S1400. Steps after step S1400 are similar to those in FIG. 2.

Next, effects of the drowsiness determination device 100 of the second modification will be described.

Figure 9:
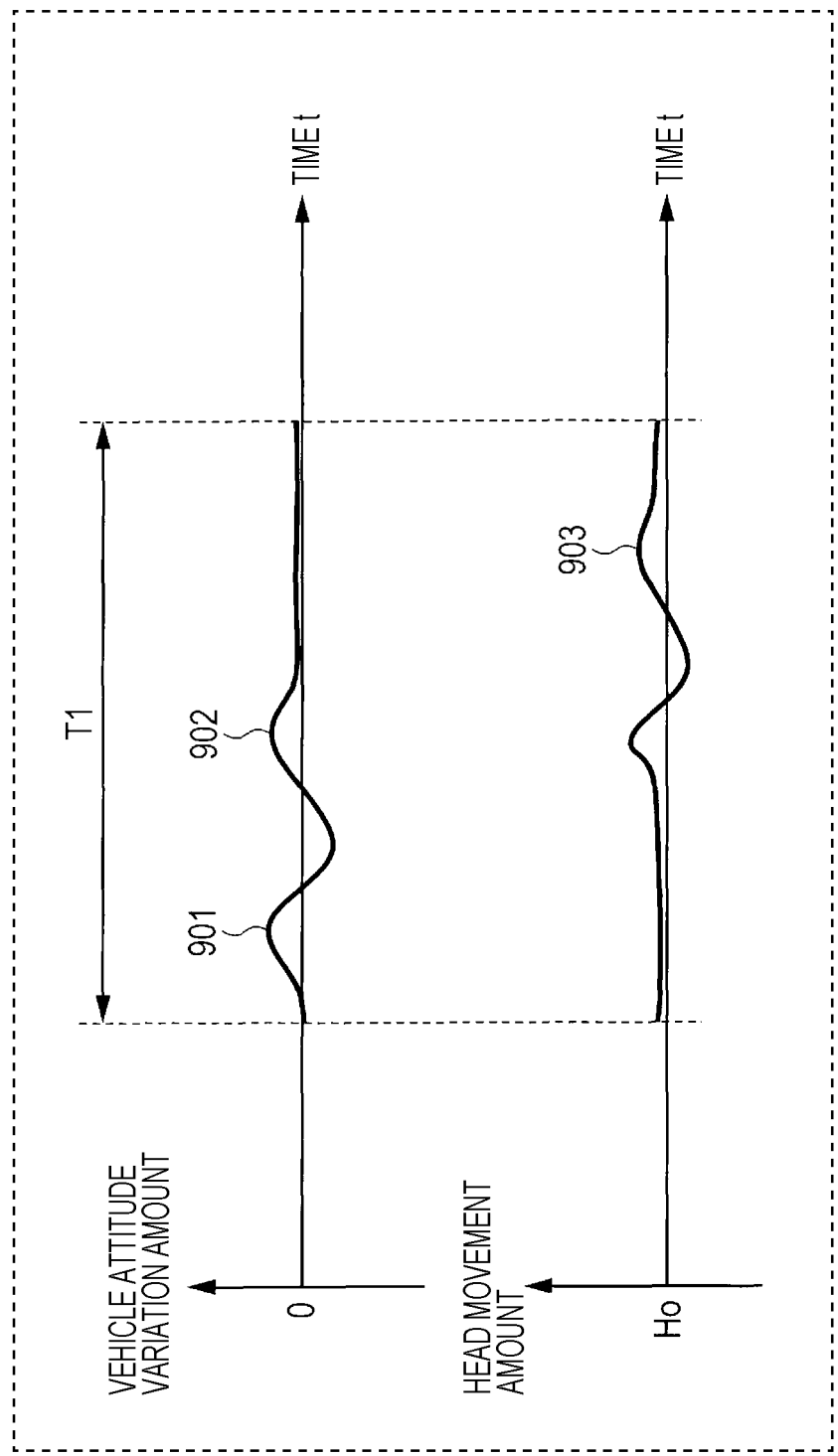
FIG. 9 is a time chart showing an example of temporal variations in the amount of variation in the vehicle attitude and the amount of movement of the occupant head of the second modification.

FIG. 9 is a time chart showing an example of temporal variations in the amount of variation in the vehicle attitude and the amount of movement of the occupant head of the second modification.

When the vehicle attitude does not significantly vary but rather repeatedly varies to a small extent, the determination unit 120 stores a waveform indicating temporal variations in the amount of the variation in the vehicle attitude and having multiple mountainous portions indicating approximately the same amount of variation, as shown in FIG. 9. Since the occupant head also repeatedly moves to a small extent in such a manner to follow the variation in the vehicle attitude, the determination unit 120 stores a waveform indicating temporal variations in the amount of the movement of the head and having multiple mountainous portions indicating approximately the same amount of movement. Note that the determination unit 120 need not store a waveform indicating the amount of variation or movement and only has to store at least information required to calculate a cross-correlation value.

In this case, each amount of variation or movement is approximately the same. For this reason, if drowsiness is determined using the peak value of the amount of variation or movement, the determination unit 120 may erroneously recognize that the second mountainous portion 903 indicating the amount of the movement of the head corresponds to the first mountainous portion 901 indicating the amount of variation in the vehicle attitude, although the second mountainous portion 903 corresponds to the second mountainous portion of 902, and thus may erroneously determine drowsiness.

On the other hand, the drowsiness determination device 100 of the second modification calculates the delay time TD on the basis of the cross-correlation between the amount of the variation in the vehicle attitude and the amount of the movement of the head. By using the delay time TD thus calculated, the drowsiness of the occupant can be accurately determined.

While the drowsiness determination device 100 uses the amount of movement when the head of the occupant is inclined with respect to the upper body thereof, as the amount of the movement of the head, the amount of movement of any other type may be used in the present disclosure. For example, the amount of movement of the entire upper body of the occupant may be used as the amount of movement of the head.

While, in the above description, the drowsiness determination device 100 determines whether the occupant is drowsy, on the basis of vehicle information indicating the amount of variation in the vehicle attitude with respect to the road surface and head information indicating the amount of movement of the occupant head with respect to the predetermined position, drowsiness may be determined on the basis of any other information. For example, a drowsiness determination device 100b may determine whether the occupant is drowsy, on the basis of vehicle information indicating the amount of variation in the vehicle attitude with respect to the road surface and body information indicating the amount of movement of the upper body (shoulder or the like) of the occupant with respect to a predetermined position. In this case, the drowsiness determination device 100b can be implemented in a similar manner by replacing the head information with body information in the above description. Further, a drowsiness determination device 100c may determine whether the occupant is drowsy, on the basis of body information indicating the amount of movement of the upper body (shoulder or the like) of the occupant with respect to a predetermined position and head information indicating the amount of movement of the occupant head with respect to a predetermined position. In this case, the drowsiness determination device 100c can be implemented in a similar manner by replacing the vehicle information with body information in the above description.

While, in the above description, the pitch direction with respect to the road surface is used as the direction of variation, the roll direction or yaw direction with respect to the road surface may be used as the direction of variation. Even in this case, similar effects can be obtained.

The present disclosure is useful as a drowsiness determination device and method that can accurately determine the drowsy state of the occupant.

Any of the modifications may be combined with any of the embodiments.

The functions of the elements of the drowsiness determination system 1 and drowsiness determination device 100 can be implemented by a computer program.

Figure 10:
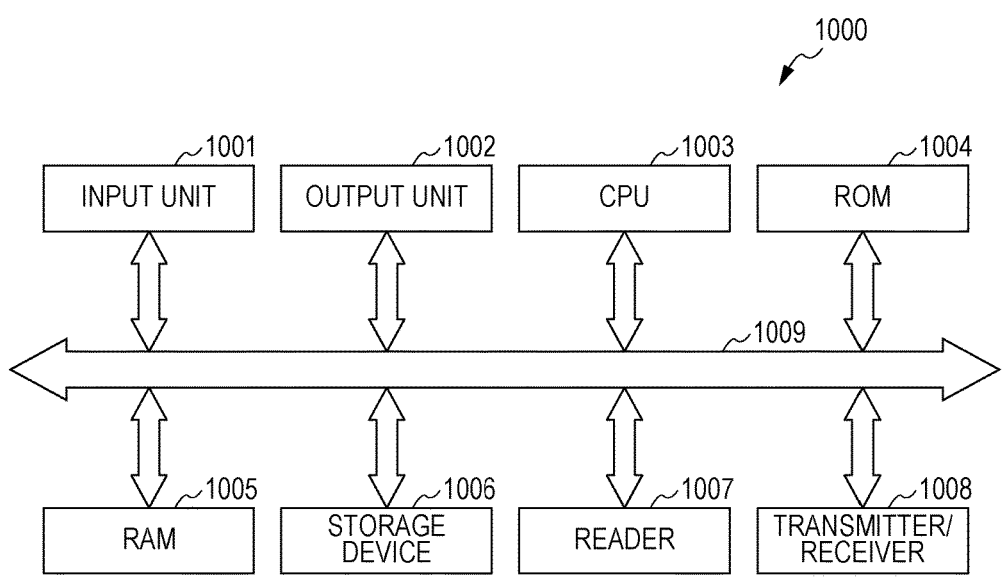
FIG. 10 is a block diagram showing an example hardware configuration of the drowsiness determination systems and drowsiness determination devices of the embodiments of the present disclosure.

FIG. 10 is a drawing showing the hardware configuration of a computer that implements the functions of the elements on the basis of a program. A computer 1000 includes an input device 1001 such as input buttons or touchpad, an output device 1002 such as a display or speaker, a central processing unit (CPU) 1003, a read-only memory (ROM) 1004, a random access memory (RAM) 1005, a storage device 1006 such as a hard disk drive or solid-state drive (SSD), a reader 1007 that reads information from a storage medium such as a digital versatile disk read-only memory (DVD-ROM) or universal serial bus (USB) memory, and a transmitter/receiver 1008 that performs communication through a network. The respective devices are connected through a bus 1009.

The reader 1007 reads a program for implementing the functions of the devices from a recording medium and stores the program in the storage device 1006. Alternatively, the transmitter/receiver 1008 communicates with a server connected to the network, downloads a program for implementing the functions of the devices from the server, and stores the program in the storage device 1006.

The CPU 1003 copies the program stored in the storage device 1006 to the RAM 1005, and sequentially reads commands included in the program from the RAM 1005 and executes the commands. Thus, the functions of the devices are implemented. When the program is executed, information obtained in the processes described in the first embodiment is stored in the RAM 1005 or storage device 1006 and used as necessary.

What is claimed is:

1. A drowsiness determination device comprising:
   a receiver, which in operation, receives vehicle information indicating an amount of variation in an attitude of a vehicle with respect to a road surface and body information indicating an amount of displacement movement of an upper body or a head of an occupant from a predetermined position in response to the variation in the attitude of the vehicle; and
   a determiner, which in operation, determines whether the occupant is drowsy, based on the vehicle information and the body information,
   wherein the determiner determines that the occupant is drowsy, when the vehicle attitude varies while moving in a traveling direction, the occupant upper body or the occupant head moves in a same direction as the traveling direction and a delay time between a first timing when the vehicle attitude has varied and a second timing when the occupant upper body or the occupant head has moved is longer than a first predetermined time,
   wherein at least one of the receiver and the determiner is included in a processor,
   wherein the displacement movement is a change in distance away from the predetermined position, and wherein the change in distance is measured by a movement sensor.

2. The drowsiness determination device of claim 1, wherein the determiner determines whether the occupant is drowsy, using a plurality of drowsiness levels corresponding to ranges of the delay time.

3. The drowsiness determination device of claim 1, wherein if the determiner determines that the occupant is drowsy, the determiner controls an alarm to be executed for awaking the occupant.

4. The drowsiness determination device of claim 1, wherein the delay time is a time corresponding to a time difference between a timing when the amount of variation in the vehicle attitude has reached a peak and a timing when the amount of displacement movement of the occupant upper body or the occupant head has reached a peak.

5. The drowsiness determination device of claim 1, wherein the determiner determines whether the occupant is drowsy, when an operation input to a vehicle-mounted device is not been detected within a second predetermined time from the first timing when the vehicle attitude has varied.

6. The drowsiness determination device of claim 1, wherein the delay time is calculated based on a correlation between the amount of variation in the attitude of the vehicle and the amount of displacement movement of the upper body or the head of the occupant.

7. A method for determining drowsiness, comprising:
receiving vehicle information indicating an amount of variation in an attitude of a vehicle with respect to a road surface and body information indicating an amount of displacement movement of an upper body or a head of an occupant from a predetermined position in response to the variation in the attitude of the vehicle;
determining whether the occupant is drowsy, based on the vehicle information and the body information; and
determining that the occupant is drowsy, when the vehicle attitude varies while moving in a traveling direction, the occupant upper body or the occupant head moves in a same direction as the traveling direction and a delay time between a first timing when the vehicle attitude has varied and a second timing when the occupant upper body or the occupant head has moved is longer than a predetermined time,
wherein the displacement movement is a change in distance away from the predetermined position, and
wherein the change in distance is measured by a movement sensor.

8. A computer-readable non-transitory storage medium storing a drowsiness determination program executed by a computer of a drowsiness determination device in a drowsiness determination system, the drowsiness determination device comprising an input that receives vehicle information indicating an amount of variation in an attitude of a vehicle with respect to a road surface and body information indicating an amount of displacement movement of an upper body or a head of an occupant from a predetermined position in response to the variation in the attitude of the vehicle, and a determiner that determines whether the occupant is drowsy, based on the vehicle information and the body information, the program causing the computer of the drowsiness determination device to perform
a process of determining that the occupant is drowsy, when the vehicle attitude varies while moving in a traveling direction, the occupant upper body or the occupant head moves in a same direction as the traveling direction and a delay time between a first timing when the vehicle attitude has varied and a second timing when the occupant upper body or the occupant head has moved is longer than a predetermined time,
wherein the displacement movement is a change in distance away from the predetermined position, and
wherein the change in distance is measured by a movement sensor.

9. A drowsiness determination device comprising:
a receiver, which in operation, receives body information indicating an amount of displacement movement of an upper body of an occupant from a first predetermined position in response to a variation in an attitude of a vehicle, and head information indicating an amount of displacement movement of a head of the occupant from a second predetermined position in response to the variation in the attitude of the vehicle; and
a determiner, which in operation, determines whether the occupant is drowsy, based on the body information and the head information,
wherein the determiner determines that the occupant is drowsy, when the vehicle attitude varies while moving in a traveling direction, the occupant head moves in a same direction as a direction in which the occupant upper body has moved, and a delay time between a first timing when the occupant upper body has moved and a second timing when the occupant head has moved is longer than a predetermined time,
wherein at least one of the receiver and the determiner is included in a processor.

* * * * *